US008648032B2

(12) United States Patent
Chapuis et al.

(10) Patent No.: US 8,648,032 B2
(45) Date of Patent: Feb. 11, 2014

(54) PHENOL ESTER AS PERFUMING INGREDIENT

(75) Inventors: Christian Chapuis, Mies (CH); Christian Vial, Saint-Julien (FR)

(73) Assignee: Firmenich SA, Geneva (CH)

( * ) Notice: Subject to any disclaimer, the term of this patent is extended or adjusted under 35 U.S.C. 154(b) by 57 days.

(21) Appl. No.: 13/318,579

(22) PCT Filed: May 19, 2010

(86) PCT No.: PCT/IB2010/052216

§ 371 (c)(1), (2), (4) Date: Nov. 2, 2011

(87) PCT Pub. No.: WO2010/140076

PCT Pub. Date: Dec. 9, 2010

(65) Prior Publication Data

US 2012/0045408 A1 Feb. 23, 2012

(30) Foreign Application Priority Data

Jun. 4, 2009 (WO) .................. PCT/IB2009/052364

(51) Int. Cl.

| | |
|---|---|
| ***A61K 8/92*** | (2006.01) |
| ***A61K 8/37*** | (2006.01) |
| ***A61Q 13/00*** | (2006.01) |
| ***A61Q 19/10*** | (2006.01) |
| ***A61Q 5/02*** | (2006.01) |
| ***A61Q 15/00*** | (2006.01) |
| ***A61Q 5/06*** | (2006.01) |
| ***A61L 9/01*** | (2006.01) |
| ***C11D 3/50*** | (2006.01) |

(52) U.S. Cl.
USPC ............... 512/21; 424/65; 424/70.1; 510/102

(58) Field of Classification Search
USPC ....................... 424/65, 70.1; 510/102; 512/21
See application file for complete search history.

(56) References Cited

U.S. PATENT DOCUMENTS 4,596,671 A 6/1986 Mookherjee et al. ......... 426/538
2008/0274944 A1* 11/2008 Margot et al. .................. 512/26
2010/0021413 A1 1/2010 McGee et al. ............... 424/76.2
2010/0087524 A1* 4/2010 Haiber et al. ................ 514/533

FOREIGN PATENT DOCUMENTS

| | | | |
|---|---|---|---|
| CA | 1 196 283 | A | 11/1985 |
| CN | 101274891 | A | 10/2008 |
| EP | 0 056 500 | A2 | 7/1982 |
| JP | 2002-187886 | A | 7/2005 |
| WO | WO 2008/055372 | A1 | 5/2008 |

OTHER PUBLICATIONS

International Search Report and Written Opinion of the International Searching Authority, Application No. PCT/IB2010/052216, dated Aug. 6, 2010.
Einhorn, "Esters of Phenols," Journal of the Chemical Society, Abstracts, 110(I):33 (1915).
Godineau et al., "Multicomponent Radical Processes: Synthesis of Substituted Piperidiones," J. Am. Chem. Soc., 129:12662-12663 (2007).
Nagase et al., "Ti-direct, powerful, stereoselective aldol-type additions of esters and thioesters to carbonyl compounds: application to the synthesis and evaluation of lactone analogs ofjasmone perfumes," Org. Biomol. Chem., 5:151-159 (2007).
Perfume and Flavor Chemicals, 1969, Montclair, New Jersey, Nos. 1164, 2491, 2499, 2500, 2504, 2508 and 2607.

* cited by examiner

*Primary Examiner* — David J Blanchard
*Assistant Examiner* — Nicole Babson
(74) *Attorney, Agent, or Firm* — Winston & Strawn LLP

(57) ABSTRACT

The present invention relates to the field of perfumery. More particularly, it concerns the use as perfuming ingredients of certain phenol esters of formula

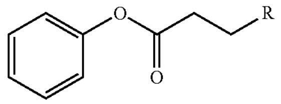

(I)

wherein R represents a $C_{2-6}$ branched alkyl group or a $C_{2-6}$ linear or branched alkenyl group or cyclopropyl containing hydrocarbon group. The present invention concerns also the compositions or articles containing such compounds.

19 Claims, No Drawings

PHENOL ESTER AS PERFUMING INGREDIENT

This application is a 371 filing of International Patent Application PCT/IB2010/052216 filed May 19, 2010.

TECHNICAL FIELD

The present invention relates to the field of perfumery. More particularly, it concerns the use of some phenol esters, as defined herein in the description, as perfuming ingredients. Moreover, the present invention comprises also the embodiments wherein the invention's compound is part of a perfuming composition or of a perfuming consumer product.

PRIOR ART

Some phenol esters are know from the prior art as having odor or taste of potential interest for the perfumery industry. One may cite those listed in reference texts such as the book by S. Arctander (Perfume and Flavor Chemicals, 1969, Montclair, N.J., USA), which are the No 1164, 2491, 2499, 2500, 2504, 2508 and 2607. All these materials are characterized by notes of the sweet/honey/balsamic and/or floral and/or fruity type.

The phenyl 3-methyl-butanoate has been reported (see *J. Chem. Soc*, Abstracts, 1915, 110, 33) as having an ethereal (i.e. floral sweet) and unpleasant odor.

Some of the invention's compounds are known from the prior art, but none of them has been reported or suggested as having potentially an odor or even less as being potentially a perfuming ingredient. For example, the phenyl 4-pentenoate is mentioned, e.g. see *J. Am. Chem. Soc* 2007, 129, 12662, as intermediate in a radical process to obtain piperidiones. The phenyl 4-methyloctanoate is also known in the prior art, see CN 101274891 or CA 2008:1196283, and said ester is mentioned as a chemical intermediate in the synthesis of some derivatives of the 3-methylheptanoic acid.

However as mentioned above, these prior art documents do not report or suggest any organoleptic properties of the compounds of formula (I), or any use of said compounds in the field of perfumery.

DESCRIPTION OF THE INVENTION

We have now surprisingly discovered that a compound of formula

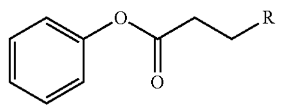

(I)

wherein R represents a $C_{2-6}$ branched alkyl group or a $C_{2-6}$ linear or branched alkenyl group or cyclopropyl containing hydrocarbon group;

can be used as perfuming ingredient, for instance to impart animal odor notes of the castoreum and/or costus type.

For the sake of clarity, by the expression "cyclopropyl containing hydrocarbon group", or the similar, it is meant the normal meaning understood by a person skilled in the art, i.e. a hydrocarbon group comprising a cyclopropyl moiety.

According to a particular embodiment of the invention, R represents a $C_3$ or $C_6$ branched alkyl group or a $C_{2-4}$ linear or branched alkenyl group or cyclopropyl containing hydrocarbon group, like vinyl or cyclopropyl. According to a particular embodiment of the invention, R represents a $C_2$, $C_3$ or $C_4$ linear or branched alkenyl group.

According to a particular embodiment of the invention, R represents a $C_2$, $C_3$ or $C_4$ linear or branched alk-1-eneyl group, such as a vinyl group.

As specific examples of the invention's compounds, one may cite, as non-limiting example, phenyl 4-pentenoate, which possesses a fresh and natural animal/castoreum note, reminding very closely of the natural Castoreum oil. In fact, this compound is a valid substitute for natural, or synthetic reconstitutions, of castoreum oil the uses of which are more and more restricted due to various reasons.

As other example, one may cite phenyl 4-methyloctanoate, which has an animal/costus note with a leathery aspect.

As other specific, but non-limiting, examples of the invention's compounds, one may cite the following ones in Table 1:

TABLE 1

Invention's compounds and their odor properties

| Compound structure and name | Odor notes |
|---|---|
| 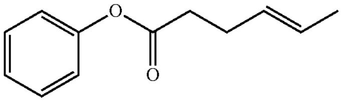 phenyl (E)-hex-4-enoate | Costoreum, civette, slightly ciste. |
| 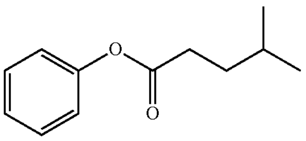 phenyl 4-methylpentanoate | Costus, slightly animal, butyric and fruity notes. |

According to a particular embodiment of the invention, the compounds of formula (I) are phenyl 4-pentenoate or phenyl (E)-hex-4-enoate.

In fact, the invention's compounds are lacking, or do not possess significant floral notes. In addition, the odor of the invention's compounds is also lacking, or does not possess significant, pungent and/or honey and/or floral type notes, which are also characteristic of some of the prior art compounds. Said differences lend the invention's compounds and the prior art compounds to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's compound as defined above;

ii) at least one ingredient selected from the group consisting of a perfumery carrier and a perfumery base; and iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualitat, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:

i) as perfuming ingredient, at least one compound of formula (I), as defined above; and ii) a fine or functional perfumery base;

is also an object of the present invention.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "fine or functional perfumery base" we mean here a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the fine or functional perfumery base do not warrant a more detailed description here, which in any case would not be exhaustive, the skilled person being able to select them on the basis of his general knowledge and according to the nature and the desired effect of said product.

Non-limiting examples of suitable fine or functional perfumery base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.1% to 10% by weight, or even more, of the compounds of the invention based on the weight of the composition into which they are incorporated. Concentrations lower than these, such as in the order of 0.01% to 5% by weight, can be used when these compounds are incorporated into perfumed articles, percentage being relative to the weight of the article.

The invention's compounds can be prepared according to a method involving the addition of an adequate carboxylic acid chloride to phenol, or vice versa. A person skilled in the art knows how to best perform said reaction.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of Compounds of Formula (I)

A) Phenyl 4-pentenoate

4-Pentenoyl chloride (8.16 g, 69.1 mmol) was added dropwise to sodium phenoxide (8.02 g, 69.1 mmol) in THF (160 ml) at 20° C. After 24 hours at 20° C. $H_2O$ (100 ml) was added and the aqueous phase was extracted with $Et_2O$ (3×200 ml). The organic phase was washed with $NaHCO_3$ (2×200 ml), brine (2×200 ml) to neutrality, then dried ($Na_2SO_4$), filtered, concentrated and bulb-to-bulb distilled to afford the desired title ester in 90% yield. B.p.: 70° C./0.04 mbar.

$^1$H-NMR: 7.37 (t, J=6.8, 2H); 7.22 (t, J=6.8, 1H); 7.08 (d, J=6.8, 2H); 5.95-5.86 (m, 1H); 5.15 (d, J=17.5, 1H); 5.08 (d, J=10.7, 1H); 2.67 (t, J=7.5, 2H); 2.51 (q, to J=7.5, 2H).

$^{13}$C-NMR: 171.5 (s); 150.7 (s); 136.3 (d); 129.4 (2d); 125.8 (d); 121.6 (2d); 115.9 (t); 33.6 (t); 28.9 (t).

B) Phenyl 4-methyloctanoate

In a 100 ml three necked round bottom flask were placed 9.4 g of phenol (0.1 mole) and 17.65 g of 4-methyl-octanoyl chloride (0.1 mole). After dissolution of phenol, the mixture was slowly heated from room temperature to 100° C. in order to see a regular evolution of HCl. After 2 hours at 100° C., the mixture was flushed with nitrogen and cooled to room temperature.

The crude reaction mixture was directly purified by flash chromatography ($SiO_2$, Hexane:$Et_2O$ 4:1) and bulb to bulb distillation ($Eb_{0.27}$=130-140° C.) to give 21.80 g (yield=93.2%) of pure phenyl 4-methyloctanoate.

$^1$H-NMR: 0.91 (t, J=7, 3H); 0.94 (t, J=7, 3H); 1.12-1.41 (m, 6H); 1.56 (m, 2H); 1.80 (m, 1H); 2.56 (m, 2H); 7.07 (d, J=7, 2H); 7.22 (t, J=7, 1H); 7.37 (dd, $J_1$=$J_2$=7, 2H)

$^{13}$C-NMR: 14.1 (q); 19.3 (q); 22.9 (t); 29.2 (t); 31.9 (t); 32.2 (t); 36.4 (t); 32.4 (d); 121.6 (2×d); 125.7 (d); 129.4 (2×d); 150.9 (s); 172.5 (s)

C) Phenyl 4-methylpentanoate

4-Methylpentanoyl chloride (3.0 g, 22.3 mmol) was added dropwise to phenol (2.1 g, 22.3 mmol). After 3 hours, $H_2O$ was added and the reaction mixture was extracted with $Et_2O$. The organic phase was washed with $NaHCO_3$, then brine to neutrality, then dried ($Na_2SO_4$), concentrated and bulb-to-bulb distilled to afford the title compound in 88% yield.

Bp: 100° C./0.15 mbar.

$^1$H-NMR: 7.36 (tt, J=8, 2, 2H); 7.21 (tt, J=7.4, 1, 1H); 7.08 (dq, J=1, 8, 2H); 2.56 (t, J=7, 2H); 1.68 (m, 3H); 0.97 (d, J=7, 6H).

$^{13}$C-NMR: 172.5 (s); 150.8 (s); 129.4 (2d); 125.7 (d); 121.6 (2d); 33.7 (t); 32.5 (t); 27.7 (d); 22.3 (2q).

D) Phenyl 4-methylhexanoate

Obtained according to the method described for C), using 4-methylhexanoyl chloride; yield=85% yield.

Bp: 100° C./0.1 mbar.

$^1$H-NMR: 7.37 (tt, J=8, 2, 2H); 7.21 (tt, J=7.4, 1, 1H); 7.07 (dq, J=1, 8, 2H); 2.55 (dq, JJ=6.2, 9.5, 2H); 1.81 (m, 1H); 1.57 (m, 1H); 1.42 (m, 2H); 1.22 (m, 1H); 0.93 (d, J=6.5, 3H); 0.91 (t, J=7.3, 3H).

$^{13}$C-NMR: 172.8 (s); 150.9 (s); 129.6 (2d); 125.7 (d); 121.6 (2d); 34.1 (d); 32.3 (t); 31.5 (t); 29.2 (t); 18.9 (q); 11.4 (q).

E) (E)-Phenyl hex-4-enoate

Obtained according to the method described for C), using hex-4-enoyl chloride; yield=85% yield.

Bp: 90° C./0.15 mbar.

$^1$H-NMR: 7.38 (tt, J=8, 2, 2H); 7.22 (tt, J=7.4, 1, 1H); 7.07 (dq, J=1, 8, 2H); 5.54 (m, 2H); 2.61 (t, J=7, 2H); 2.43 (q, J=7, 2H); 1.69 (d, J=7, 3H).

$^{13}$C-NMR: 171.8 (s); 150.8 (s); 129.4 (2d); 128.8 (d); 126.7 (d); 125.7 (d); 121.6 (2d); 34.4 (t); 28.0 (t); 17.9 (q).

Example 2

Preparation of a Perfuming Composition

An eau de Cologne for men, having a herbaceous-woody character, was prepared by admixing the following ingredients:

| Ingredient | Parts by weight |
|---|---|
| Styrallyl acetate | 10 |
| 10%* C 10 aldehyde | 25 |

-continued

| Ingredient | Parts by weight |
|---|---|
| 10%* C 11 lenic aldehyde | 10 |
| 10%* C 12 aldehyde | 10 |
| Hexylcinnamic aldehyde | 200 |
| 10%* MNA aldehyde | 10 |
| 10%* Ambrox ®[1] | 10 |
| 50%* Methyl N-(7-hydroxy-3,7-dimethyl-1-octenyl) anthranilate | 70 |
| Armoise essential oil | 55 |
| Bergamote essential oil | 55 |
| Citronellol | 10 |
| Citronellyl Nitrile | 5 |
| Coumarin | 75 |
| 10%* Cumin essential oil | 30 |
| Dihydromyrcenol | 30 |
| Tarragon | 15 |
| Eugenol | 50 |
| Florol ®[2] | 70 |
| 70%** Galaxolide ®[3] | 260 |
| Geraniol essential oil | 10 |
| Geranium Bourbon | 30 |
| Iralia ®[4] | 100 |
| Lavandin Grosso | 50 |
| Lilial ®[5] | 70 |
| Lilyflore ®[6] | 30 |
| Crystal moss | 30 |
| Muscenone ®[7] Delta | 60 |
| Patchouli | 300 |
| Phenethylol | 40 |
| Polysantol ®[8] | 20 |
| Rosemary essential oil | 15 |
| Sclareolate ®[9] | 80 |
| Vanilline | 5 |
| Vertofix ®[10] Coeur | 210 |
| Vetyver Bourbon | 50 |
| | 2100 |

*in dipropyleneglycol

**in isopropyle myristate

[1] (−)-(8R)-8,12-epoxy-13,14,15,16-tetranorlabdane; origin: Firmenich SA, Geneva, Switzerland

[2] tetrahydro-2-isobutyl-4-methyl-4(2H)-pyranol; origin : Firmenich SA, Geneva, Switzerland

[3] 1,3,4,6,7,8-hexahydro-4,6,6,7,8,8-hexamethyl-cyclopenta-g-2-benzopyrane; origin: International Flavors & Fragrances, USA

[4] mixture of methyl ionones; origin: Firmenich SA, Switzerland

[5] 3-(4-tert-butylphenyl)-2-methylpropanal; origin: Givaudan-Roure SA, Vernier, Switzerland

[6] 2,5-dimethyl-2-indanmethanol; origin: Firmenich SA, Switzerland

[7] 3-methyl-(4/5)-cyclopentadecenone; origin: Firmenich SA, Switzerland

[8] 3,3-dimethyl-5-(2,2,3-trimethyl-3-cyclopenten-1-yl)-4-penten-2-ol; origin: Firmenich SA, Switzerland

[9] propyl (S)-2-(1,1-dimethylpropoxy)propanoate; origin: Firmenich SA, Switzerland

[10] methyl cedryl ketone; origin: International Flavors & Fragrances, USA

The addition of 50 parts by weight of natural Castoreum oil imparted a clearly pronounced natural animal/castoreum connotation.

When, instead of the natural compound, or even instead of a synthetic reconstitution thereof, there was added 100 parts by weight of phenyl-4-pentenoate to the above-described eau de Cologne, the effect obtained was very similar, although a bit less natural. Overall, the invention's compound was judged an excellent substitute to the natural oil or its reconstitutions.

Example 3

Preparation of a Perfuming Composition

A perfuming composition, of the synthetic castoreum type, was prepared by admixing the following ingredients:

| Ingredient | Parts by weight |
|---|---|
| 10%* Phenylpropyl acetate | 20 |
| 10%* Acetophenone | 70 |
| Benzoic acide | 500 |
| Benzylic alcool | 20 |
| 10%* Phenylpropyl alcool | 50 |
| 10%* Salicylic aldehyde | 25 |
| 1%* 4-(4-Hydroxy-1-phenyl)-2-butanone | 40 |
| 10%* Borneol | 25 |
| 10%* Carvacrol | 25 |
| 10%* 2-Methoxy-4-methylphenol | 20 |
| 10%* Eugenol | 5 |
| 10%* Isoeugenol | 10 |
| 1%* Guaiacol | 100 |
| Gurjun Baume | 200 |
| 10%* Helional ®[1] | 35 |
| Methylphenylcarbinol | 25 |
| Ethyl Guaiacol | 60 |
| 10%* Ortho-Cresol | 45 |
| 10%* Phenethylol | 15 |
| 4-Ethylphenol | 125 |
| 10%* 4-Methylphenol | 85 |
| 0.1%* Methyl salicylate | 50 |
| | 1550 |

*in dipropyleneglycol

[1] 3-(1,3-benzodioxol-5-yl)-2-methylpropanal; origin: Firmenich SA, Geneva, Switzerland The addition of 50 parts by weight of phenyl-4-pentenoate to the above-described synthetic castoreum, clearly reinforced the animal notes of the original composition and imparted also a natural connotation to the fragrance.

What is claimed is:

1. A method to confer, enhance, improve or modify the odor properties of a perfuming composition or of a perfumed article, which method comprises adding to the composition or article an effective amount of a compound of formula

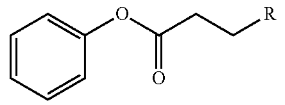

(I)

wherein R represents a $C_{2-6}$ branched alkyl group or a $C_{2-6}$ linear or branched alkenyl group or cyclopropyl containing hydrocarbon group.

2. The method according to claim 1, wherein R represents a $C_2$, $C_3$ or $C_4$ linear or branched alk-1-enyl group.

3. The method according to claim 1, wherein the compound is phenyl-4-pentenoate or phenyl (E)-hex-4-enoate.

4. The method according to claim 1, wherein the compound is phenyl-4-pentenoate.

5. The method according to claim 1, wherein the compound is added in a perfuming composition comprising:

i) at least one compound of formula (I);

ii) at least one ingredient selected from the group consisting of a perfumery carrier and a perfumery base; and iii) optionally at least one perfumery adjuvant.

6. The method of claim 1 wherein the compound is added in an amount effective to provide an animal odor note of the castoreum or costus type.

7. The method according to claim 1, wherein the compound is present in a perfuming consumer product comprising:

i) at least one compound of formula (I); and ii) a fine or functional perfumery base.

8. The method according to claim 7, wherein the fine or functional perfumery base is a perfume, a fabric care product, a body-care product, an air care product or a home care product.

9. The method according to claim 7, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

10. A perfuming composition comprising:

i) at least one compound of formula

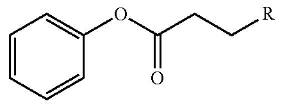

(I)

wherein R represents a $C_{2-6}$ branched alkyl group or a $C_{2-6}$ linear or branched alkenyl group or cyclopropyl containing hydrocarbon group;

ii) at least one ingredient selected from the group consisting of a perfumery carrier and a perfumery base; and iii) optionally at least one perfumery adjuvant.

11. A perfuming composition according to claim 10, wherein R represents a C2, C3 or C4 linear or branched alk-1-enyl group.

12. A perfuming composition according to claim 10, wherein the compound is phenyl-4-pentenoate or phenyl (E)-hex-4-enoate.

13. A perfuming composition according to claim 10, wherein the compound is phenyl-4-pentenoate.

14. A perfuming consumer product comprising:

(i) at least one compound of formula

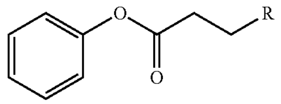

(I)

wherein R represents a $C_{2-6}$ branched alkyl group or a $C_{2-6}$ linear or branched alkenyl group or cyclopropyl containing hydrocarbon group; and (ii) a fine or functional perfumery base.

15. A perfuming consumer product according to claim 14, wherein the fine or functional perfumery base is a perfume, a fabric care product, a body-care product, an air care product or a home care product.

16. A perfuming consumer product according to claim 14, wherein the fine or functional perfumery base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oils or gel, a hygiene product, an air freshener, a "ready to use" powdered air freshener, a wipe, a dish detergent or hard-surface detergent.

17. A perfuming consumer product according to claim 14, wherein R represents a C2, C3 or C4 linear or branched alk-1-enyl group.

18. A perfuming consumer product according to claim 14, wherein the compound is phenyl-4-pentenoate or phenyl (E)-hex-4-enoate.

19. A perfuming consumer product according to claim 14, wherein the compound is phenyl-4-pentenoate.

* * * * *